(12) United States Patent
Jacobson et al.

(10) Patent No.: US 6,213,151 B1
(45) Date of Patent: Apr. 10, 2001

(54) MICROFLUIDIC CIRCUIT DESIGNS FOR PERFORMING FLUIDIC MANIPULATIONS THAT REDUCE THE NUMBER OF PUMPING SOURCES AND FLUID RESERVOIRS

(75) Inventors: Stephen C. Jacobson; J. Michael Ramsey, both of Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 0 days.

(21) Appl. No.: 09/557,435

(22) Filed: Apr. 25, 2000

Related U.S. Application Data (63) Continuation-in-part of application No. 09/212,217, filed on Dec. 16, 1998, now Pat. No. 6,062,261.

(51) Int. Cl.⁷ .................................................. G01N 27/26
(52) U.S. Cl. ............................................ 137/827; 137/833
(58) Field of Search .................................... 137/827, 806, 137/826, 833

(56) References Cited

U.S. PATENT DOCUMENTS

| | | | |
|---|---|---|---|
| 5,116,471 | * | 5/1992 | Chien et al. .......................... 204/453 |
| 5,126,022 | * | 6/1992 | Soane et al. .......................... 204/458 |
| 5,180,480 | * | 1/1993 | Manz .............................. 204/209 R |
| 5,328,578 | * | 7/1994 | Gordon ............................... 204/452 |
| 5,376,252 | * | 12/1994 | Ekstrom et al. .................... 204/603 |
| 5,603,351 | | 2/1997 | Cherukuri et al. . |
| 5,750,015 | * | 5/1998 | Soane et al. ........................ 204/454 |
| 5,858,187 | * | 1/1999 | Ramsey et al. ..................... 204/452 |

* cited by examiner

Primary Examiner—A. Michael Chambers
(74) Attorney, Agent, or Firm—Dann, Dorfman, Herrell and Skillman, P.C.

(57) ABSTRACT

A microfabricated device and method for proportioning and mixing biological or chemical materials by pressure- or vacuum-driven flow is disclosed. The microfabricated device mixes a plurality of materials in volumetric proportions controlled by the flow resistances of tributary reagent channels through which the materials are transported. The microchip includes two or more tributary reagent channels combining at one or more junctions to form one or more mixing channels. By varying the geometries of the channels (length, cross section, etc.), a plurality of reagent materials can be mixed at a junction such that the proportions of the reagent materials in the mixing channel depend on a ratio of the channel geometries and material properties. Such an approach facilitates flow division on the microchip without relying on techniques external to the microchip. Microchannel designs that provide the necessary flow division to accomplish valving operations using a minimum of pressure or vacuum sources are also described. In addition, microchannel designs that accomplish fluidic operation utilizing a minimal number of fluidic reservoirs are disclosed.

42 Claims, 8 Drawing Sheets

MICROFLUIDIC CIRCUIT DESIGNS FOR PERFORMING FLUIDIC MANIPULATIONS THAT REDUCE THE NUMBER OF PUMPING SOURCES AND FLUID RESERVOIRS

CROSS-REFERENCE TO RELATED APPLICATIONS

This application is a continuation-in-part of application Ser. No. 09/212,217, filed Dec. 16, 1998, now U.S. Pat. No. 6,062,261, issued May 16, 2000, the entirety of which is incorporated herein by reference.

GOVERNMENT RIGHTS STATEMENT

The U.S. Government has a paid-up license in this invention and the right in limited circumstances to require the patent owner to license others on reasonable terms as provided for by the terms of contract No. DE-AC05-00OR22725 awarded by the U.S. Department of Energy.

FIELD OF THE INVENTION

The invention relates to a microchip design for the fluidic manipulation of chemical and biological materials. More specifically, this invention relates to a microchip device in which the reagent and mixing channels are dimensioned to proportion the fluidic driving forces without the need for external schemes or multiple independent pressure sources, and to reduce the number of fluidic reservoirs needed for operability, relative to known microchip devices. Similar advantages are provided by embodiments for performing dispensing operations.

BACKGROUND OF THE INVENTION

The mixing of two or more liquid-phase materials or the dispensing of a reagent material on a microchip is accomplished by controlling the pressure (vacuum) applied to the various reservoirs or channels to drive the materials housed therein through the channels of the microchip. Heretofore, this process has required external control using individual pressure (vacuum) sources at each reservoir or channel or a pressure (vacuum) manifold to distribute appropriate pressures (vacuums). Such external sources are utilized to effect valving and mixing phenomena in the channel manifold of a microfabricated device.

Therefore, a need has arisen for a microchip that is capable of mixing sample material in various proportions and dispensing variable volumes of a sample material in which the fluid material is driven by a minimum number of pressure (vacuum) sources. In this way, excess hardware needed for a fluid transport can be minimized, and the microchip can be operated with fewer fluidic reservoirs compared to known designs.

SUMMARY OF THE INVENTION

The present invention provides a microfabricated device for liquid phase chemical and biological analysis or synthesis. A device in accordance with the invention includes a substrate on which a series of microchannels are formed. A cover plate is bonded to the substrate to close the open side of the microchannels. Reservoirs are in fluidic communication with the ends of the microchannels. The reservoirs or channels are connected to pressure (vacuum) sources for mixing and/or dispensing fluidic materials contained therein. Here and throughout this application the term "pressure" means a pressure that is either above, below, or equal to the ambient pressure conditions.

The microchip includes a series of tributary channel junctions ("tees" and/or four-way intersections) wherein at least two tributary reagent microchannels communicate with a common mixing microchannel. The tributary reagent channels have either different cross sectional areas, different lengths, or both and, therefore different flow resistances. The material in the tributary reagent channels is mixed at a channel junction depending on the ratio of the channel flow resistances. Such an approach can handle all or a portion of the flow division on the microchip without using techniques external to the microchip. The mixing of two or more materials is achieved using pressure driven transport. In accordance with another aspect of the present invention, there is provided a microfabricated device that is capable of dispensing variable volumes of a sample material. In accordance with a further aspect of this invention, the tributary channels are formed so that a reduced number of material reservoirs can be utilized when performing multiple ratio assays or reactions.

A first category of microfabricated devices in accordance with the present invention provides a flow division technique that utilizes a reduced number of different external pressure sources to effect microfluidic reagent mixing relative to previous devices. A second category of microfabricated devices in accordance with this invention allows dispensing of samples on a multi-port device with a reduced number of pressure sources.

BRIEF DESCRIPTION OF THE DRAWINGS

The foregoing summary, and the following detailed description, will be best understood when read in conjunction with the attached drawings, in which.

DETAILED DESCRIPTION

A microfabricated device in accordance with the present invention is described in connection with a number of embodiments. The embodiments of this invention demonstrate the mixing of two or more reagent materials by way of a series of tributary channel junctions wherein at least two tributary reagent microchannels communicate with a common mixing microchannel. The tributary reagent channels have the same cross sectional area but different lengths and, therefore different flow resistances. A comparable device could be fabricated using similar channel lengths but different cross-sectional areas or a combination of the two strategies. The amount of reagent supplied by each tributary channel is dependent upon the ratio of the channel lengths and the transport properties of the materials within the channels. Variations in such parameters can be taken into account in designing structures such as described in this application, provided that the parameters are known to the designer. If parameters for some materials are not known, then a device can be designed to minimize the influence of such material on the functioning of the device. For the embodiments described hereinbelow, it is assumed that the transport properties are uniform throughout the structure, although it is recognized that such is not a necessary assumption in order to make an operative device.

In a first embodiment, material in the tributary reagent channels is mixed at a common junction. The amount of reagent supplied by each tributary channel is dependent upon the ratio of the channel lengths. The design approach for this embodiment can handle all the flow division on the microchip without using techniques external to the microchip. The mixing of two or more materials is achieved using pressure driven transport of the fluidic materials.

In a second embodiment of this invention, there is provided a microfabricated device employing a valve that is capable of dispensing variable quantities of a sample material. In accordance with a third embodiment of this invention, a microfabricated device is provided for performing a plurality of dilution experiments with a minimized number of reagent and diluent material reservoirs and a reduced number of pressure sources.

Volumetric Proportioning

Figure 1:
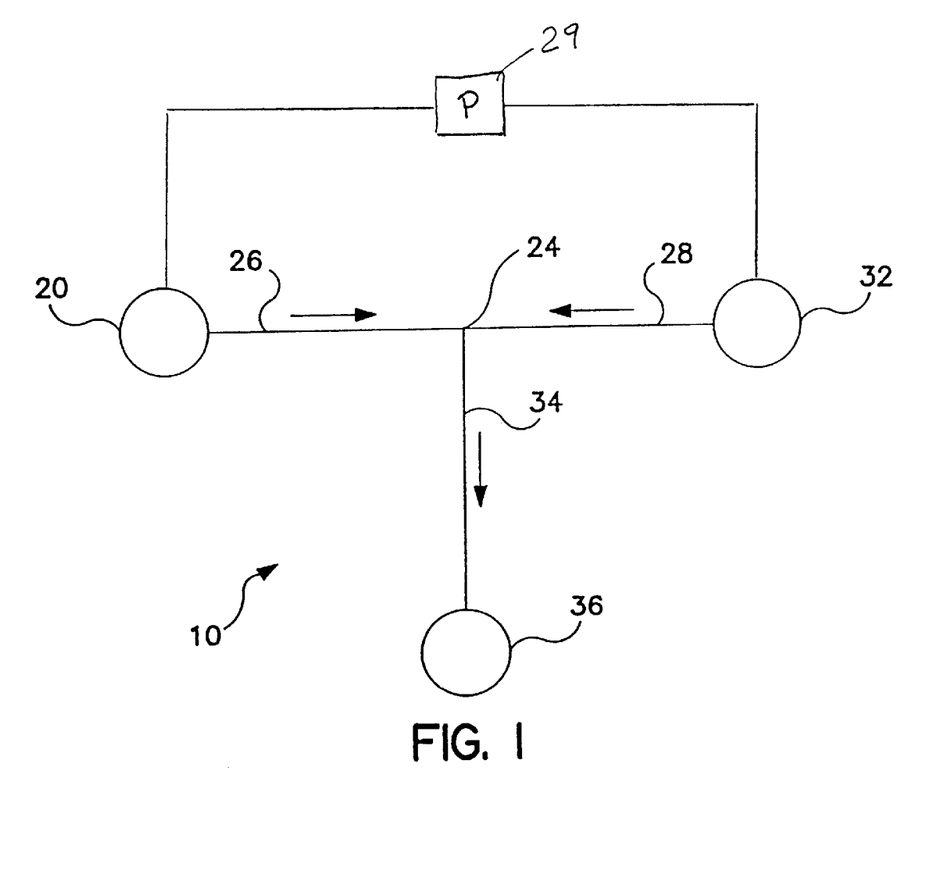
FIG. 1 is a schematic diagram showing a mixing junction in accordance with this invention.

Referring now to FIG. 1, a mixing junction or "tee" 10 includes a sample reservoir 20, buffer reservoir 32, sample channel 26, buffer channel 28, a mixing channel 34, and waste reservoir 36. When a single pressure source 29 is applied to the sample reservoir 20 and buffer reservoir 32 to provide a pressure differential relative to waste reservoir 36, the fluidic materials from the sample reservoir and the buffer reservoir flow into and are mixed in the tee junction 24 in a ratio that is inversely proportional to the flow resistances of the sample channel 26 and buffer channel 28. Alternatively, a pressure source below ambient pressure (vacuum) can be applied to the waste reservoir 36 to draw material from the sample reservoir 20 and buffer reservoir 32 to mix at the tee junction 24. When the sample channel 26 and buffer channel 28 have the same cross-sectional area, the flow resistance is directly proportional to the channel lengths. Thus, when the sample and buffer channels have the same lengths and the same cross-sectional areas, the sample and buffer materials are transported to and mixed in equal proportions at junction 24 under the assumption of homogeneous material properties. When the sample and buffer channels have different lengths, the sample is diluted by the buffer material in a ratio that is proportional to the length of the buffer channel relative to the combined lengths of the sample and buffer channels. Alternatively, the cross-sectional areas of the sample and buffer channels can be dimensioned to provide the desired mixing proportions because the flow resistance of the respective channel is inversely proportional to the cross-sectional area of the channel. Of course, it is also contemplated that the channel resistance can be selected by adjusting both the channel lengths and the channel cross-sectional areas to provide the desired transport and mixing of the sample and buffer materials.

Figure 2:
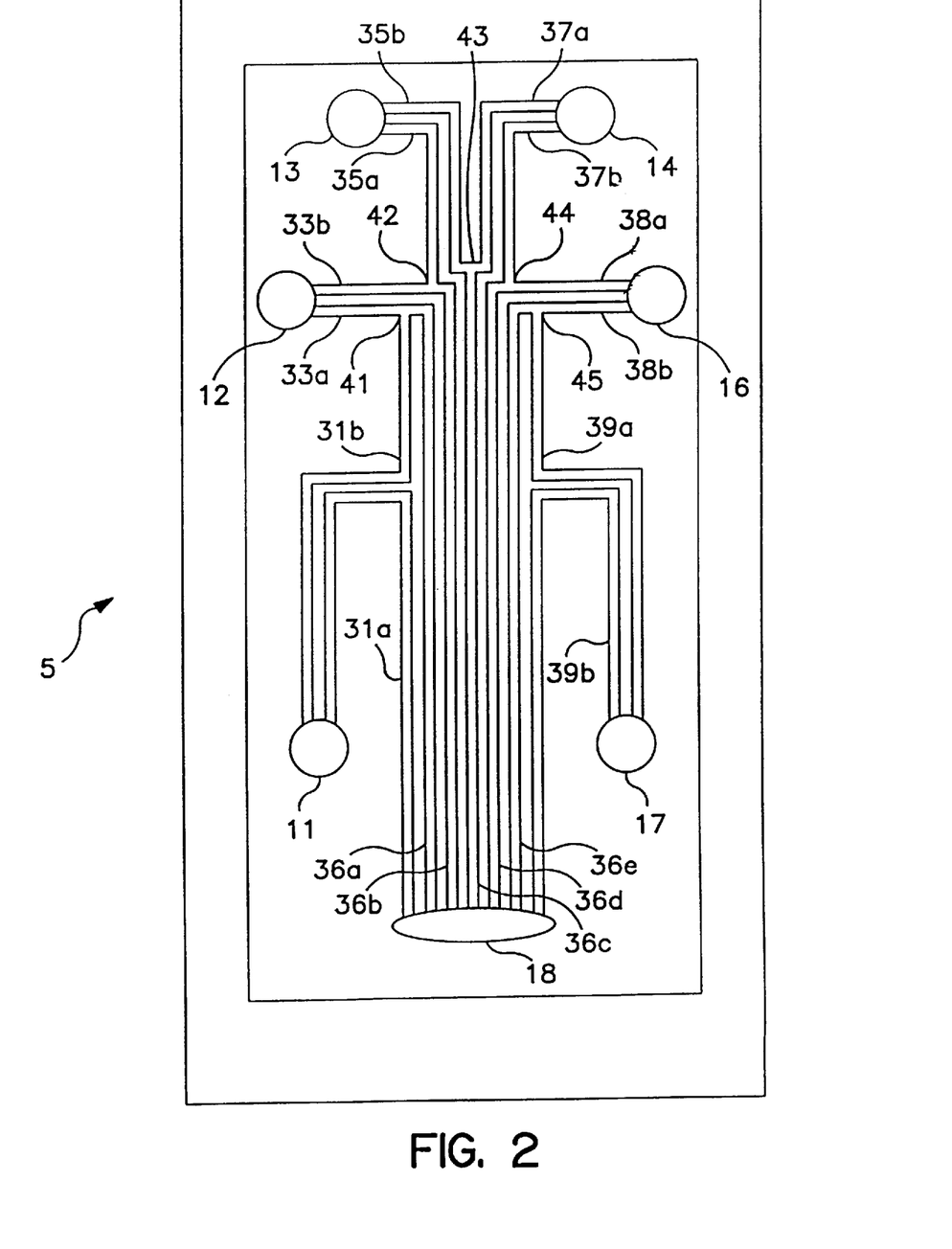
FIG. 2 is a schematic diagram of a fluidic microchip for mixing reagents in accordance with the present invention.

Referring now to FIG. 2, there is shown a fluidic microchip in accordance with this invention. The microfabricated device 5 includes a first buffer reservoir 11, a first sample reservoir 12, a second buffer reservoir 13, a second sample reservoir 14, a third buffer reservoir 16, a third sample reservoir 17, and a waste reservoir 18. A first buffer channel 31a connects the first buffer reservoir 11 with the waste reservoir 18. A second buffer channel 31b connects the first buffer reservoir 11 with a first sample channel 33a that is in fluid communication with the first sample reservoir 12. The intersection of the second buffer channel 31b and first sample channel 33a forms a "tee" junction 41 with a first waste channel 36a that is in fluid communication with the waste reservoir 18. In like manner the second buffer reservoir 13 is connected to the first and second sample reservoirs 12 and 14 and to the waste reservoir 18 through channels 33b, 35a, 35b, 36b, 36c, and 37a. Further, the third buffer reservoir 16 is connected to the second and third sample reservoirs 14 and 17 and to the waste reservoir 18 through channels 37b, 38a, 38b, 39a, 36d, and 36e. The dimensions of the channels 31b, 33a, 33b, 35a, 35b, 37a, 37b, 38a, 38b, and 39a are selected to provide respective flow resistances that result in desired mixing ratios of the various sample and buffer materials at the corresponding junctions 41, 42, 43, 44, and 45, for transport to the waste reservoir 18 along the waste channels 36a, 36b, 36c, 36d, and 36e, respectively.

The mixing of two or more materials contained in the microfabricated channels of a microchip device according to this invention is achieved using pressure driven transport. A pressure source (not shown) is connected to the sample and buffer reservoirs 11, 12, 13, 14, 16, 17 to provide a pressure differential relative to the waste reservoir 18 to transport the materials through the microchip channel manifold. Alternatively, a sub-ambient pressure source can be connected to the waste reservoir 18 to provide a pressure differential relative to the sample and buffer reservoirs 11, 12, 13, 14, 16, 17 to draw sample material through the microchannel manifold.

Figure 2A:
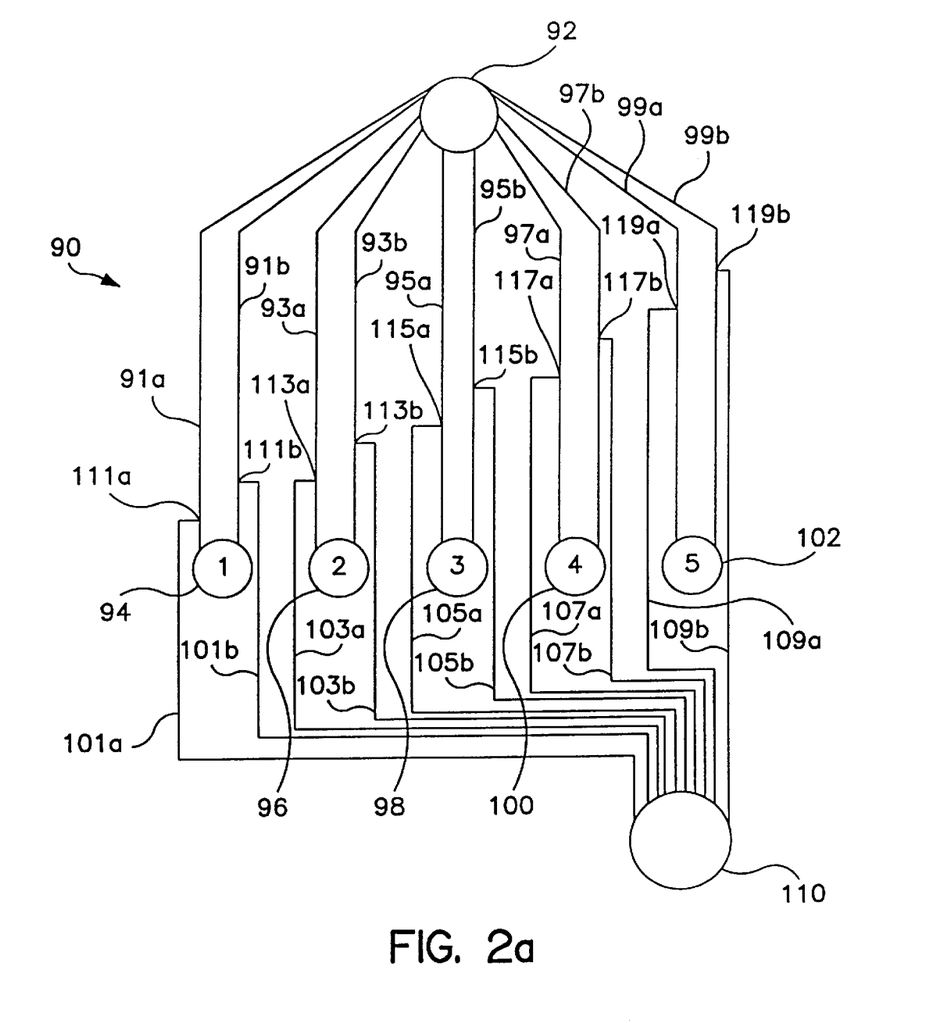
FIG. 2a is a schematic diagram of an alternative embodiment of the fluidic microchip shown in FIG. 2.

Referring now to FIG. 2a, an alternative embodiment of a microchip device in accordance with the present invention is shown having multiple sets of mixing junctions configured for minimizing the number of material reservoirs. The device 90 includes a single sample reservoir 92, a plurality of buffer reservoirs 94, 96, 98, 100, and 102, and a waste reservoir 110. The sample material is loaded into the sample reservoir 92. A pressure source (not shown for simplicity) is connected to sample reservoir 92 and the buffer reservoirs 94, 96, 98, 100, and 102 to provide a pressure differential relative to waste reservoir 110. Alternatively, a sub-ambient pressure source can be connected to waste reservoir 110. A common buffer, reagent, or various buffers or reagents are loaded into the buffer reservoirs 94–102. Respective pairs of sample channels 91a, 91b, 93a, 93b, 95a, 95b, 97a, 97b, and 99a, 99b interconnect the sample reservoir 92 to each of the plurality of buffer/reagent reservoirs 94–102. Corresponding pairs of mixing channels 101a, 101b, 103a, 103b, 105a, 105b, 107a, 107b, and 109a, 109b interconnect each sample channel with the waste reservoir 110. The mixing channels intersect the sample channels at mixing junctions 111a, 111b, 113a, 113b, 115a, 115b, 117a, 117b, and 119a, 119b, respectively.

The arrangement in FIG. 2a allows a large number of simultaneous, fixed dilutions of the sample material to be performed with one or more buffer solutions. The cross-sectional areas and lengths of the channel segments forming the mixing junctions are dimensioned to provide mixing of the sample and buffer materials in different, preselected proportions at each of the mixing junctions. In this way, the device 90 minimizes the number of reservoirs required to do the multiple dilutions of a single sample within a two dimensional layout, i.e., without crossing of channels. In general, to perform N dilutions, N/2+2 reservoirs are required. The value is rounded up to the next higher integer if N is an odd number. In a variation of the embodiment shown in FIG. 2a, the plurality of buffer reservoirs are combined into a single reservoir by using sufficiently small vertical access conduits (vias) through the microchannel coverplate and a buffer reservoir having a sufficiently large cross section to access the vias. Alternatively, vias could be used to communicate between multiple layers of microchannels to allow the reduction of the plurality of buffer reservoirs into a single reservoir. The multiple layers of microchannels would allow channels to cross over the tops of each other similar to the constructs used in multilayer printed circuit boards.

Variable Volume Valve

Figure 3:
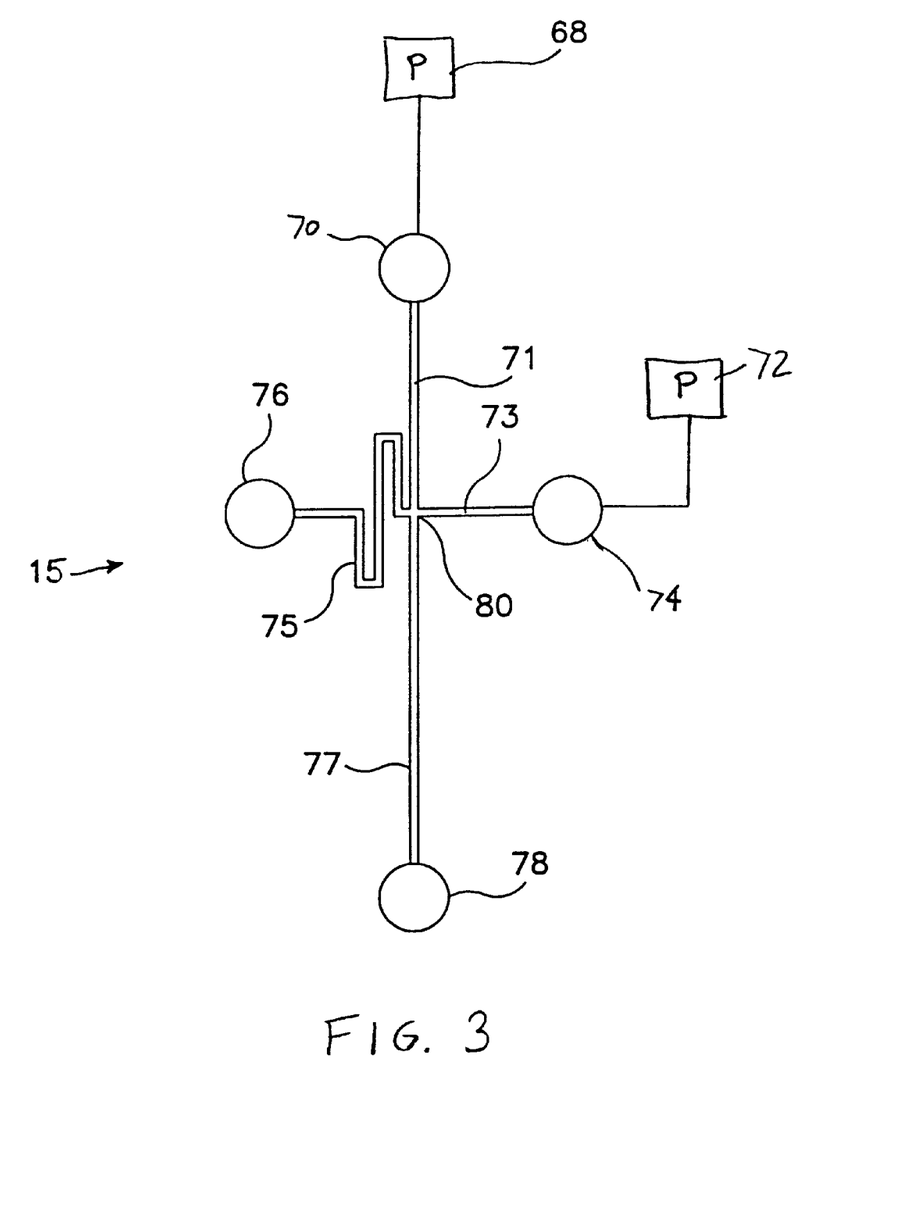
FIG. 3 is a schematic diagram of a microchip in accordance with the present invention that is configured for microfluidic valving.

A schematic of a microchip 15 according to the present invention that demonstrates valving is depicted in FIG. 3. The microchip 15 includes a sample reservoir 70, a buffer reservoir 74, a first waste reservoir 76, and a second waste reservoir 78. A sample channel 71 has a first end in fluidic communication with the sample reservoir 70. A buffer channel 73 has a first end in fluidic communication with the buffer reservoir 74. A first waste channel 75 has one end in fluidic communication with the first waste reservoir 76 and a second waste channel 77 has an end in fluidic communication with the second waste reservoir 78. The second ends of the four channels meet at a valving junction 80. The lengths of the various channels between the respective reservoirs and the valving junction are selected to provide predetermined flow resistance in the respective channels.

In a first operation mode, the sample reservoir 70 is connected to a first pressure source 68, and the buffer reservoir 74 is connected to a second pressure source 72. In the microchip design of FIG. 5, the valve 80 is closed when the pressures applied by these pressure sources are equal in magnitude. The first and second waste reservoirs 76, 78 are maintained at a lower pressure relative to the pressure sources 68 and 72. When valve 80 is closed, the sample material is transported only to the first waste reservoir 76. The valve 80 is actuated or opened by lowering the pressure applied to buffer reservoir 74 relative to the pressure applied to sample reservoir 70. When valve 80 is open, the sample material is transported to both first waste reservoir 76 and second waste reservoir 78. The second pressure source 72 includes means for reducing the pressure applied to buffer reservoir 74. Such pressure reducing means may include a pressure reducing valve, a pressure bleed-off valve, or a shut-off valve. The pressure reducing means can be electrically and/or computer controlled. In an embodiment where the pressure source includes a plunger device, such as in a syringe, pressure reduction is accomplished by slowing, stopping, or retracting the plunger. The relative proportions of sample material transported into the first waste channel 75 and the second waste channel 77 are determined according to the relative flow resistances of the respective channels and the relative magnitudes of the first pressure source 68 and second pressure source 72. Alternatively, the valve 80 can be opened by increasing the pressure applied to the sample reservoir 70 relative to the pressure applied to the buffer reservoir 74.

In a second operational mode, this variable volume valve is operated by applying a first sub-ambient pressure (vacuum) source to the first waste reservoir 76 and a second sub-ambient pressure (vacuum) source to the second waste reservoir 78. In the design shown in FIG. 3, these vacuum sources provide vacuums that are substantially equal in magnitude to maintain the valve 80 in a "closed" configuration. When the valve 80 is closed, the sample is transported only to the first waste reservoir 76. In this mode, the valve 80 is opened by increasing the sub-ambient pressure applied to the first waste reservoir relative to the sub-ambient pressure applied to the second waste reservoir. When the valve 80 is open, the sample material is transported to the second waste reservoir 78. Alternatively, the valve 80 can be opened by decreasing the sub-ambient pressure (vacuum) applied to the second waste reservoir 78.

Figure 4:
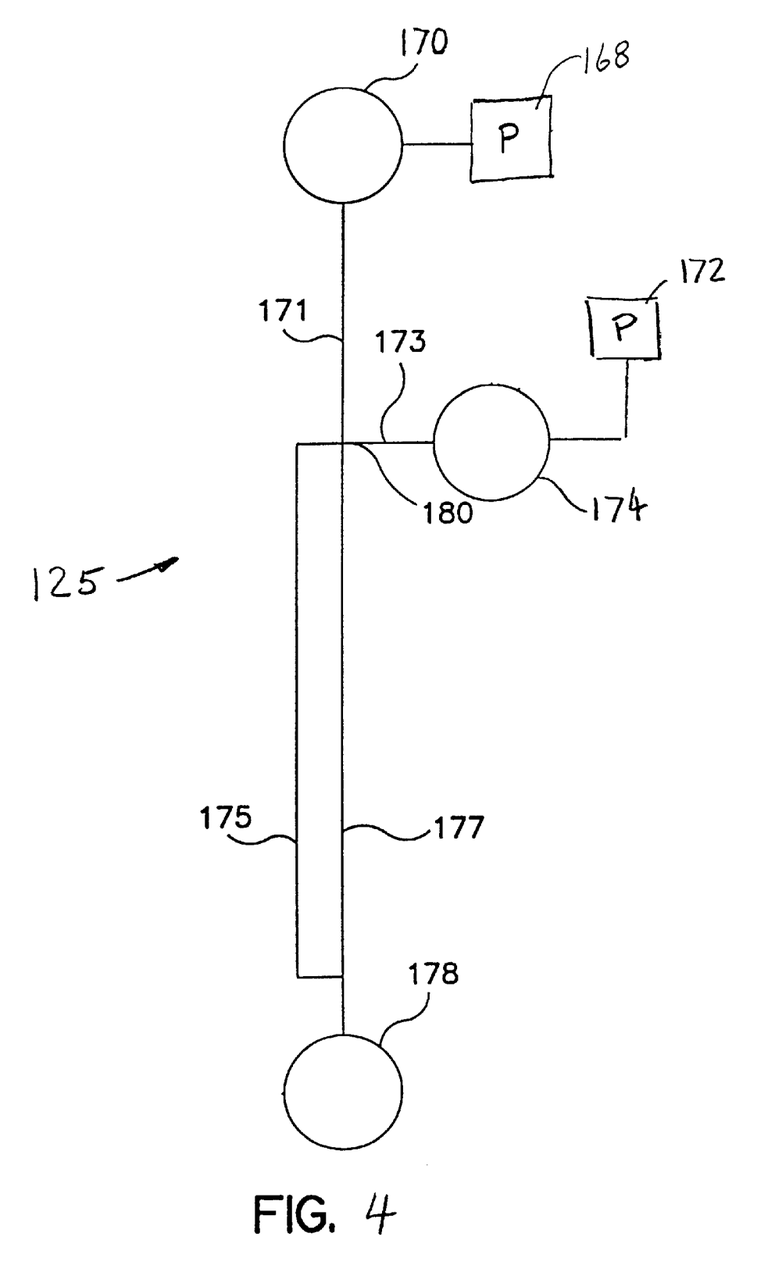
FIG. 4 is a schematic diagram of an alternative embodiment of the microchip shown in FIG. 3.

A further embodiment for valving in accordance with the present invention is shown in FIG. 4. The device 125 requires fewer fluidic reservoirs to effect valving than the embodiment shown in FIG. 3 and is actuated similar to the first operation mode of that embodiment. Microchip device 125 reduces the number of waste reservoirs to one because the waste channel 175 and analysis channel 177 transport the combined sample and buffer materials to a single waste reservoir 178. The buffer channel 173, sample channel 171, waste channel 175, and the analysis channel 177 are dimensioned so as to provide appropriate flows in the four channels that intersect at the valve junction 180. For the proper operation of the gated valve, the flow resistances of the channels are preferably designed so that the flow rate in the buffer channel 173 is greater than the flow rate in the analysis channel 177 and the flow rate in the waste channel 175 is greater than the flow rate in the sample channel 171. Similar to device 15 of FIG. 3, a first pressure source 168 is connected to the sample reservoir 170 and a second pressure source 172 is connected to the buffer reservoir 174. The valving device 125 is actuated in essentially the same manner as the device shown in FIG. 3. More specifically, when the pressure applied to buffer reservoir 174 is lowered, the valve 180 is opened, and when the pressure applied to buffer reservoir 174 is returned to its initial value, approximately equal to the pressure applied to the sample reservoir 171, the valve 180 closes. The functionality of the valving device 125 can also be accomplished by using separate pressure sources independent of the dimensions of the respective channels.

The microchip structures in FIGS. 3 and 4 can also be actuated with a combination of super-ambient and sub-ambient pressure sources and in combination with electrokinetic fluid transport as described in copending application Ser. No. 09/212,217 now U.S. Pat. No. 6,062,261.

Reagent Mixing Circuit

Figure 5:
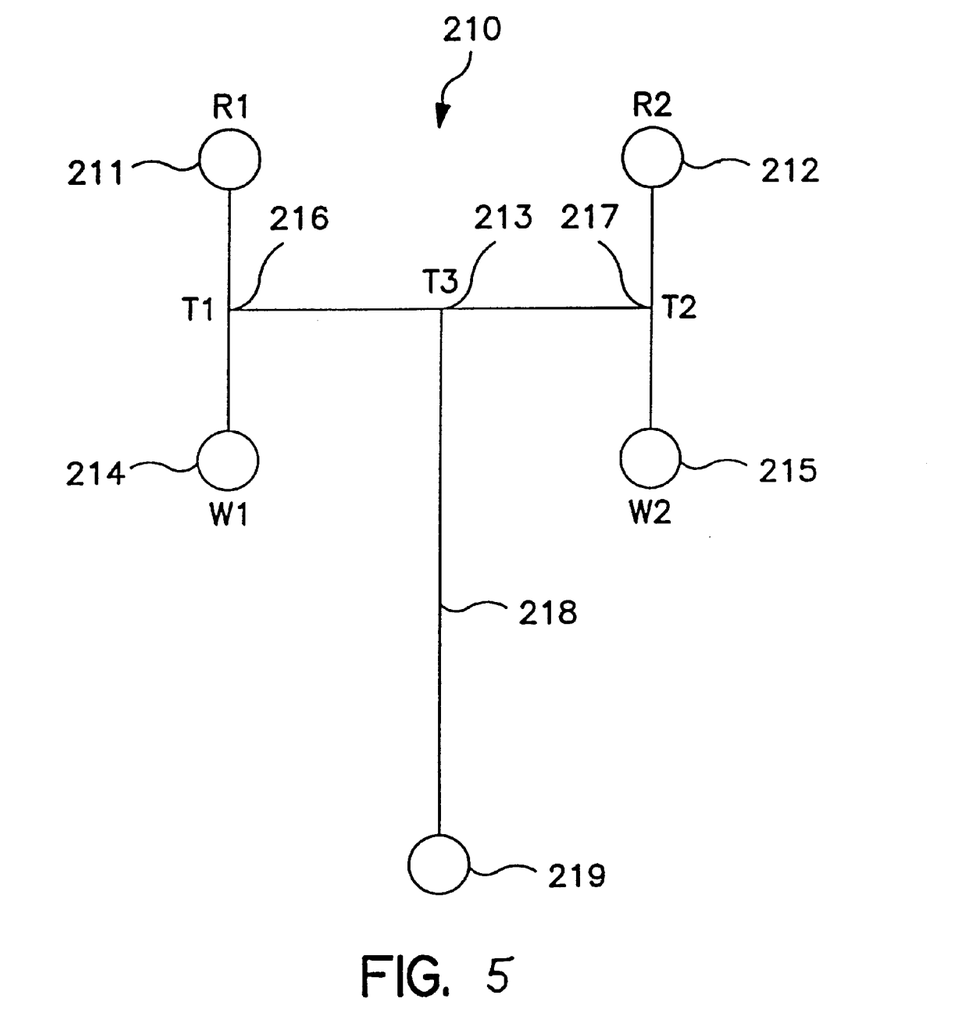
FIG. 5 is a schematic diagram of a reagent mixing circuit in accordance with another aspect of this invention.

Referring now to FIG. 5, there is shown schematically a standard reagent mixing circuit 210 for implementation on a microchip in accordance with the present invention. In the mixing circuit 210 a pressure source (not shown) is connected to R1 reservoir 211 and R2 reservoir 212. Pressure is not applied to the W1 reservoir 214, the W2 reservoir 215, or the reservoir 219. A first reagent from R1 reservoir 211 and a second reagent from R2 reservoir 212 are mixed at T3 intersection 213. In this embodiment, the W1 reservoir 214 and the W2 reservoir 215 are used as flow shunts to assist in the delivery of low flow rates of the first and second reagents to the T3 intersection 213. The use of flow shunts permits a wide range of stable mixing ratios for the reagents with minimal requirements for flow control. Without flow shunts, highly precise pressure sources would be required to reliably pump small volumes of material within the channel manifold. Alternatively, pressure sources can be applied to the W1 and W2 reservoirs to balance the flows from the R1 and R2 reservoirs and enable up to 100% flows from the R1 and R2 reservoirs toward the T3 intersection.

To deliver a small volume of the first reagent to the T3 intersection 213 using the W1 reservoir 214 as a flow shunt, the material is transported from the R1 reservoir 211, and the flow is split at the T1 intersection 216. Controlled portions of the first reagent are sent toward the T3 intersection 213 and the W1 reservoir 214. The ratio of the split portions is determined by the applied pressures and the flow resistances of the channels leading from the R1 reservoir 211 and the W1 reservoir 214. Likewise, to accurately deliver small volumes of the second reagent to the T3 intersection 213 using the W2 reservoir 215 as a flow shunt, the material transported from the R2 reservoir 212 is split at the T2 intersection 217, with a portion of the material transported toward the T3 intersection 213 and a second portion transported toward the W2 reservoir 215. This configuration allows delivery of small volumes of material from either the R1 reservoir 211 or the R2 reservoir 212 to the T3 intersection 213, where they are mixed, and avoids having to use highly precise pressure sources. This flow shunting can also be achieved by applying sub-ambient pressure sources to the waste reservoirs 214, 215, and 219.

An alternate configuration for the mixing circuit shown in FIG. 5 is to use the W1 reservoir 214 and the W2 reservoir 215 to dilute the reagent materials from the R1 reservoir 211 and the R2 reservoirs 212, respectively, prior to their being mixed at the T3 intersection 213. To dilute the material in the R1 reservoir 211 with material from the W1 reservoir 214, pressure sources are applied to both the R1 reservoir 211 and the W1 reservoir 214 to transport the materials from the respective reservoirs towards the T1 intersection 216. The amount of dilution of the first reagent by the buffer material in the W1 reservoir 214 at the T1 intersection 216 depends on the magnitudes of the pressures applied to the reservoirs and the flow resistances of the respective channels. Similarly, to dilute the material from the R2 reservoir 212 with the buffer material from the W2 reservoir 215, pressure sources are applied to both the R2 reservoir 212 and the W2 reservoir 215 to transport the materials from the respective reservoirs toward the T2 intersection 217. The amount of dilution of the second reagent by the buffer material in the W2 reservoir 215 at the T2 intersection 217 depends on the magnitudes of the pressures applied to the respective reservoirs and the flow resistances in the channels. By using the first and second buffers to dilute the first and second reagents, respectively, a wider concentration range of reagents can be reacted at the T3 intersection and studied in the reaction channel 218.

Figure 6:
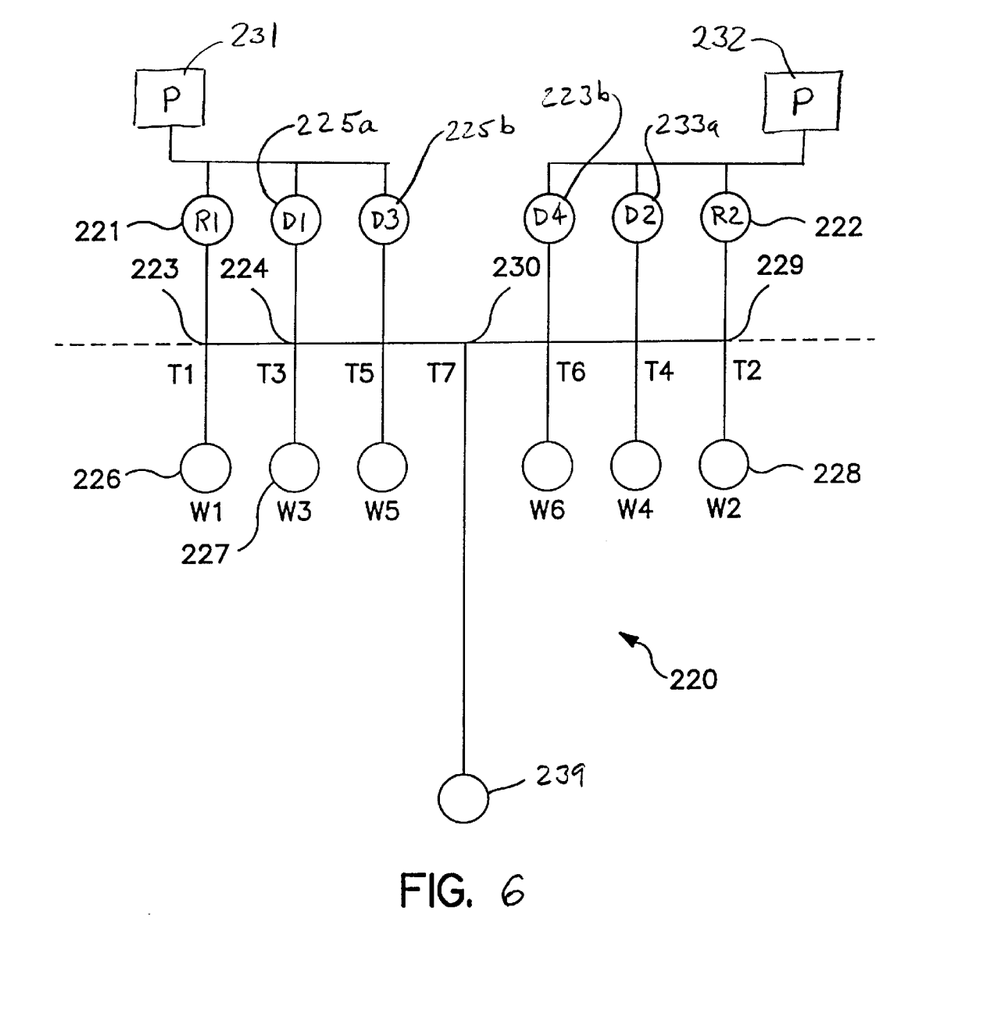
FIG. 6 is a schematic diagram of another embodiment of the reagent mixing circuit shown in FIG. 5.

Referring now to FIG. 6, there is shown a modified arrangement for the dilution/mixing circuit shown in FIG. 5. In the circuit shown in FIG. 6, multiple fluid shunts are included to provide increased dynamic range over the dilution of either the first reagent in R1 reservoir 221, the second reagent in R2 reservoir 222, or both. A first pressure source 231 is connected to R1 reservoir 221, D1 reservoir 225a and the D3 reservoir 225b. A second pressure source 232 is connected to R2 reservoir 222, D2 reservoir 233a, and D4 reservoir 223b. The flow of the first reagent through T1 intersection 223 operates just as the corresponding intersection of the embodiment shown in FIG. 5 and described above. The first and second pressure sources can be combined as a single source. The flow of the first reagent from the T1 intersection toward the T7 intersection 230 can be further diluted at the T3 intersection 224 with a first diluent held in D1 reservoir 225. W3 reservoir 227 allows a material shunting process to occur similar to that which occurs at the T1 intersection 223. This serial dilution process can continue with additional fluidic elements that comprise an input channel, an output channel, a diluent channel, and a shunting channel all connected at a four-way intersection. The reservoirs and intersections on the right hand side of the T7 intersection 230 mirror the reservoirs and intersections shown on the left hand side of that intersection. They perform similar operations, but carry out the dilution process on the second reagent which is held in R2 reservoir 222. The circuit depicted schematically in FIG. 6 allows independent control over all of the reagent, diluent, and waste (shunting) reservoirs for maximal control of the process. Each reservoir in FIG. 6 could have an independently controlled pressure source to enable the most flexible operation. In general, the diluents would be the same, but they could also be different. In an alternative arrangement to that shown in FIG. 6 and described above, sub-ambient pressure sources are applied to the waste reservoirs W1, W3, W5, W2, W4, and W6 and the main waste reservoir 239.

An operationally less complex fluid circuit that can perform a similar dilution function can be produced by making the left-hand-side and right-hand-side diluent and waste reservoirs, respectively, common. Such a device is shown in FIG. 7 and described below.

Serial Dilution Circuit

The microfluidic device of the present invention can be further embodied as a serial diluter. In a serial diluter according to this invention, a series of channels, tees, and intersections are configured for mixing two reagents (a sample and a buffer) in a series of preselected ratios. The desired dilutions correspond to the fluid flow in the various channels of the microchip. Therefore, a microchip for implementing this aspect of the present invention is designed by analyzing the various channels as an equivalent electrical circuit. Each channel or circuit branch has a resistance designed to provide a desired flow therethrough. The sample and buffer materials are transported through the various microchannels in direct proportion to the equivalent current flow. FIG. 7 shows a preferred microfluidic circuit 810 for a serial diluter in accordance with this aspect of the present invention.

Figure 7:
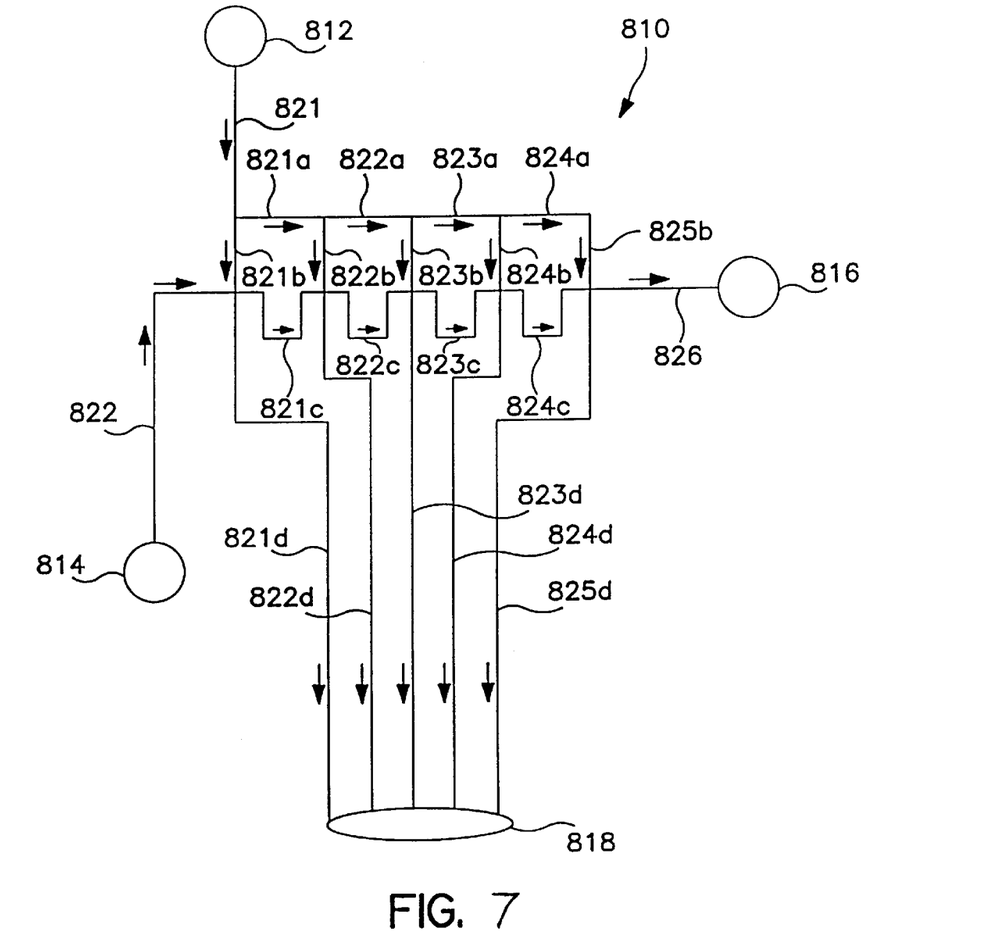
FIG. 7 is a schematic diagram of a fluidic microchip for performing multiple serial dilutions in accordance with another embodiment of this invention.

Referring now to FIG. 7, the serial diluter circuit 810 includes a buffer reservoir 812 for holding a buffering material or other diluent, a sample reservoir 814 for holding a sample material, a first waste reservoir 816, and a second waste reservoir 818. A main buffer channel 821 in fluid communication with the buffer reservoir 812 is formed for carrying the buffer material. A sample channel 822 is in fluid communication with the sample reservoir 814 for carrying the sample material.

A plurality of buffer channel extensions 821a, 822a, 823a, and 824a extend in series from the buffer channel 821. A set of buffer branch channels 821b, 822b, 823b, 824b, and 825b each branch off from the buffer channel extensions 821a, 822a, 823a, and 824a, respectively, at selected locations relative to the intersection with the main buffer channel 821. The sample channel 822 interconnects with the buffer branch channel 821b at a preselected distance from the intersection with the first buffer extension channel 821a. A mixing channel 821c interconnects with the buffer branch channel 821b at the point of intersection with sample channel 822. A series of mixing channels 822c, 823c, and 824c extend from the other end of mixing channel 821c. A set of analysis channels 821d, 822d, 823d, 824d, and 825d branch off from the mixing channels 821c, 822c, 823c, and 824c, respectively, at selected locations relative to the intersection with the branch channel 821b. In the embodiment shown in FIG. 7, the analysis channels branch off at respective ends of the mixing channels. The analysis channels have different lengths relative to one another and are in fluid communication with the second waste reservoir 818. A waste channel 826 interconnects the end of mixing channel 824c with the first waste channel 816.

When a pressure is applied to the buffer reservoir 812 and the sample reservoir 814 that is elevated relative to the waste reservoirs 816 and 818, the buffer material is transported along buffer channel 821 into buffer channel extension 821a and buffer branch channel 821b. The buffer material is similarly transported from buffer branch channel 821b into mixing channel 821c. Arrows indicate the buffer flow direction in the drawing. Simultaneously, the sample material is transported along sample channel 822 into mixing channel 821c and analysis channel 821d as indicated by the arrows in FIG. 7. The sample material is diluted with the buffer material in mixing channel 821c, whereas the sample material in analysis channel 821d is at the same concentration as the sample material in sample channel 822, i.e., it is undiluted. This same flow pattern develops if a sub-ambient pressure (vacuum) is applied to the waste reservoirs 816 and 818 relative to the buffer reservoir 812 and sample reservoir 814. Alternatively, waste reservoir 816 and 818 can be combined into a single reservoir to further simplify the structure.

As the process continues, the buffer material in buffer extension channel 821a is split between buffer extension channel 822a and buffer branch channel 822b. The buffer material in branch channel 822b flows into mixing channel 822c and the diluted sample material in mixing channel 821c is split between mixing channel 822c and analysis channel 822d. The diluted sample material from mixing channel 821c is further diluted in mixing channel 822c, whereas the diluted sample material in analysis channel 822d is at the same concentration as the diluted sample material in mixing channel 821c.

It can be readily appreciated that further splitting and dilution of the sample and buffer materials is accomplished in a similar fashion with buffer extension channels 823a and 824a, buffer branch channels 823b, 824b, and 825b, mixing channels 823c and 824c, and analysis channels 823d, 824d, and 825d. In the embodiment shown in FIG. 7, there are five analysis channels, but the series of channel extensions, channel branches, mixing channels, and analysis channels can continue for as many dilutions as needed for a particular process.

In the embodiment of FIG. 7, the channels are formed with essentially the same cross-sectional areas. The channel flow resistance is increased by lengthening the channel or decreased by shortening the channel during design and fabrication of the microchip. Use of relatively narrow cross sections for the mixing channels is preferred because it allows rapid equilibration of the mixed fluid streams. In a preferred mode of operation, the velocity of the fluid streams is below a limit that allows efficient mixing of the materials in the mixing channels.

In any of the embodiments described above, the pressure source can be embodied as any type of device that is known to those skilled in the art to be capable of applying a pressure to the respective reservoir or channel. Also, in any of the embodiments described above, the increasing or decreasing of the pressure source to the reservoir or channel can be embodied as any type of device that is known to those skilled in the art to be capable of such. In a preferred embodiment, the pressure source is a syringe device or a regulated pressure source that is connected to the device reservoirs with appropriate fittings. The sub-ambient pressure (vacuum) source can be embodied as any type of device that is known to those skilled in the art including vacuum pumps or a suction device such as a syringe device operated in a withdraw mode. The pressure does not have to be constant for the device to operate. As described above, the pumping of the fluidic materials can be accomplished with any combination of pressure and vacuum sources, and may even include electrokinetic pumping means, to create pressure differentials using intrachannel connections to effect the flow of the fluidic materials in a desired direction and with a desired flow velocity. The fabrication and operability of these intrachannel connections (membranes) are described in copending application Ser. No. 09/244,914, the entirety of which is incorporated herein by reference.

In view of the foregoing disclosure, it can be seen that the microfabricated device in accordance with the present invention readily provides microfluidic proportioning. Such functionality is useful in analyzing chemical and biological reactions such as kinetics studies requiring the combination of materials in precise volumes. The microfabricated device disclosed herein enables the on-chip mixing of materials in different proportions using channels having different flow resistances. The microfabricated device includes one or more channel junctions or "tees" having sample and buffer reagent channels that meet at a mixing junction. By having tributary channels with the same cross sectional area but different lengths, the materials traveling therethrough, can be mixed at a junction depending on the ratio of the channel lengths, because the flow resistances of the microfabricated channels are directly proportional to the channel length. Microfabricated channels having different cross-sectional areas could also effectively proportion samples, because the microchannel resistance is inversely proportional to cross-sectional area. As such, handling of the flow division on the microchip can be accomplished by properly dimensioning the channels of the microfabricated device without using techniques external to the microchip. In this way, the number of pressure sources needed to operate a microfluidic device can be greatly reduced. Furthermore, by appropriate arrangement and dimensioning of the microchannels and their interconnections, the number of sample, buffer, and waste reservoirs needed to perform multiple dilutions of a sample material can be significantly reduced. In addition, the devices described herein can be operated using a combination of pressure and vacuum sources operatively connected to the reservoirs or channels or in combination with functionally equivalent electrokinetic fluid transport mechanisms as described in our co-pending application Ser. No. 09/212, 217 now U.S. Pat. No. 6,062,261.

The terms and expressions which have been employed are used as terms of description and not of limitation. There is no intention in the use of such terms and expressions of excluding any equivalents of the features shown and described or portions thereof. For example channel resistance can be varied by altering channel width or height as well as length to facilitate compact microfluidic designs. It is recognized, however, that various modifications such as channel dimension, location, and arrangement are possible within the scope of the invention as claimed.

That which is claimed is:

1. An apparatus for effecting microfluidic manipulation comprising:
   a first reservoir adapted for containing a first material;
   a second reservoir adapted for containing a second material;

a third reservoir adapted for containing a third material;

a first channel having a first end in fluidic communication with said first reservoir;

a second channel having a first end in fluidic communication with said second reservoir;

a third channel having a first end in fluidic communication with said third reservoir;

said first, second, and third channels having respective second ends that are interconnected to form a junction; and transport means operatively connected to said first and second channels, or to said third channel, for effecting transport of the first and second materials from said first and second reservoirs toward said third reservoir;

wherein the lengths, cross-sections, or combinations thereof, of the first, second, and third channels are dimensioned to provide mixing of the first and second materials at said junction in a first ratio upon application of the transport means to said first and second channels or to said third channel.

2. The apparatus of claim 1 wherein said first, second, and third channels have the same cross-sectional dimension and the lengths of said channels are proportioned to provide mixing of the first material and the second material at said junction in the first ratio.

3. The apparatus of claim 1 wherein said transport means comprises a pressure source operatively connected to said first and second channels for providing a pressure differential relative to said third channel.

4. The apparatus of claim 1 wherein said transport means comprises a sub-ambient pressure source operatively connected to said third channel for providing a pressure differential relative to said first and second channels.

5. Apparatus as set forth in claim 1 comprising:

a fourth reservoir adapted for containing a fourth material;

a fourth channel having a first end in fluidic communication with said fourth reservoir;

a fifth channel having a first end in fluidic communication with said second reservoir; and a sixth channel having a first end in fluidic communication with said third reservoir;

said fourth, fifth, and sixth channels having respective second ends that are interconnected to form a second junction;

wherein said transport means is operatively connected to said fourth channel for effecting transport of the fourth material from said fourth reservoir toward said third reservoir, and the lengths, cross-sections, or combinations thereof, of the fourth, fifth, and sixth channels are dimensioned to provide mixing of the second and fourth materials at said second junction in a second ratio upon application of the transport means to said second and fourth channels or to said third channel.

6. Apparatus as set forth in claim 5 wherein the first and fourth reservoirs are formed as a single reservoir.

7. Apparatus as set forth in claim 1 comprising:

a plurality of first channels each having a first end in fluidic communication with said first reservoir;

a plurality of second channels having a first end in fluidic communication with said second reservoir; and a plurality of third channels each having a first end in fluidic communication with said third reservoir;

wherein each combination of first, second, and third channels has respective second ends that are respectively interconnected to form a plurality of junctions and the lengths, cross-sections, or combinations thereof, of the each of the combinations of first, second, and third channels are dimensioned to provide mixing of the first and second fluidic materials in a plurality of ratios upon application of the transport means for effecting transport toward said third reservoir such that a desired mixing ratio is provided at each of said plurality of junctions.

8. The apparatus of claim 7 wherein said pluralities of first, second, and third channels have the same cross-sectional dimension and the lengths of said channels are formed to provide the mixing of the first fluidic material and the second fluidic material at said plurality of junctions in the plurality of ratios.

9. The apparatus of claim 7 wherein said second reservoir comprises a plurality of second reservoirs.

10. The apparatus of claim 9 wherein pairs of said plurality of second channels have their first ends in fluidic communication with respective ones of said plurality of second reservoirs.

11. The apparatus of claim 1 wherein said first reservoir comprises a plurality of first reservoirs, said second reservoir comprises a plurality of second reservoirs, said first channel comprises a plurality of first channels each having a first end in fluidic communication with respective ones of said plurality of first reservoirs, said second channel comprises a plurality of second channels each having a first end in fluidic communication with respective ones of said plurality of second reservoirs, and said third channel comprises a plurality of third channels each having a first end in fluidic communication with said third reservoir; said pluralities of first, second, and third channels each having respective second ends that are respectively interconnected to form a plurality of junctions; and the lengths, cross-sections, or combinations thereof, of the each of the pluralities of first, second, and third channels are dimensioned to provide mixing of the first and second fluidic materials in a plurality of ratios upon application of the transport means to said reservoirs such that a desired mixing ratio is provided at each of said plurality of junctions.

12. An apparatus for effecting microfluidic manipulations comprising:

a first reservoir adapted for containing a first material;

a second reservoir adapted for containing a second material;

a third reservoir adapted for containing a third material;

a fourth reservoir adapted for containing a fourth material;

a first channel having a first end in fluidic communication with said first reservoir;

a second channel having a first end in fluidic communication with said second reservoir;

a third channel having a first end in fluidic communication with said third reservoir;

a fourth channel having a first end in fluidic communication with said fourth reservoir;

said first, second, third, and fourth channels having respective second ends that are interconnected to form a junction; and transport means operatively connected to said first channel and to said second channel for effecting transport of the first and second materials from said first and second reservoirs toward said third and fourth reservoirs;

wherein the lengths, cross-sections, or combinations thereof, of the first, second, third, and fourth channels are dimensioned such that (i) the second material is transported toward said third and fourth reservoirs and said first material is transported toward said third reservoir when said transport means is in a first state, and (ii) said first material is transported toward said fourth reservoir when said transport means is in a second state different from said first state.

13. The apparatus of claim 12 wherein said transport means comprises a first source of pressure operatively connected to said first channel and a second source of pressure operatively connected to said second channel for effecting transport of the first and second materials from said first and second reservoirs toward said third and fourth reservoirs;

wherein the lengths, cross-sections, or combinations thereof, of the first, second, third, and fourth channels are dimensioned such that (i) the second material is transported toward said third and fourth reservoirs and said first material is transported toward said third reservoir when pressures are applied to said first and second channels, and (ii) said first material is transported toward said fourth reservoir when the pressure applied to said second channel by said second pressure source is different relative to that applied in condition (i).

14. The apparatus of claim 13 wherein the pressures applied to said first and second channels in condition (i) are substantially the same.

15. The apparatus of claim 13 or 14 wherein the pressure applied to said second channel in condition (ii) is less than that applied to said first channel.

16. An apparatus for effecting microfluidic manipulations comprising:

a first reservoir adapted for containing a first material;

a second reservoir adapted for containing a second material;

a third reservoir adapted for containing a third material;

a fourth reservoir adapted for containing a fourth material;

a first channel having a first end in fluidic communication with said first reservoir;

a second channel having a first end in fluidic communication with said second reservoir;

a third channel having a first end in fluidic communication with said third reservoir;

a fourth channel having a first end in fluidic communication with said fourth reservoir;

said first, second, third, and fourth channels having respective second ends that are interconnected to form a junction; and transport means operatively connected to said third channel and to said fourth channel for effecting transport of the first and second materials from said first and second reservoirs toward said third and fourth reservoirs;

wherein the lengths, cross-sections, or combinations thereof, of the first, second, third, and fourth channels are dimensioned such that (i) the second material is transported toward said third and fourth reservoirs and said first material is transported toward said third reservoir when said transport means is in a first state, and (ii) said first material is transported toward said fourth reservoir when said transport means is in a second state different from said first state.

17. The apparatus of claim 16 wherein the transport means comprises a first sub-ambient pressure source operatively connected to said third channel and a second sub-ambient pressure source operatively connected to said fourth channel for effecting transport of the first and second materials from said first and second reservoirs toward said third and fourth reservoirs;

wherein the lengths, cross-sections, or combinations thereof, of the first, second, third, and fourth channels are dimensioned such that (i) the second material is transported toward said third and fourth reservoirs and said first material is transported toward said third reservoir when the sub-ambient pressures are applied to said third and fourth channels, and (ii) said first material is transported toward said fourth reservoir when the sub-ambient pressure applied to said fourth channel by said second sub-ambient pressure source is different relative to that applied in condition (i).

18. The apparatus of claim 17 wherein the sub-ambient pressures applied to said third and fourth channels in condition (i) are substantially the same.

19. The apparatus of claim 17 or 18 wherein the sub-ambient pressure applied to said fourth channel in condition (ii) is lower than that applied to said third channel.

20. An apparatus for effecting microfluidic manipulations comprising:

a first reservoir adapted for containing a first material;

a second reservoir adapted for containing a second material;

a third reservoir adapted for containing a third material;

a first channel having a first end in fluidic communication with said first reservoir;

a second channel having a first end in fluidic communication with said second reservoir;

a third channel having a first end in fluidic communication with said third reservoir;

a fourth channel having a first end in fluidic communication with said third reservoir;

said first, second, third, and fourth channels having respective second ends that are interconnected to form a junction; and transport means operatively connected to said first channel and to said second channel for effecting transport of the first and second materials from said first and second reservoirs toward said third reservoir;

wherein the lengths, cross-sections, or combinations thereof, of the first, second, third, and fourth channels are dimensioned such that (i) the second material is transported through said third and fourth channels to said third reservoir and said first material is transported through the third channel to said third reservoir when the transport means is in a first state, and (ii) said first material is transported through said fourth channel to said third reservoir when the transport means is in a second state that is different from said first state.

21. The apparatus of claim 20 wherein the transport means comprises a first source of pressure operatively connected to said first channel and a second source of pressure operatively connected to said second channel for effecting transport of the first and second materials from said first and second reservoirs toward said third reservoir;

wherein the lengths, cross-sections, or combinations thereof, of the first, second, third, and fourth channels are dimensioned such that (i) the second material is transported toward said third and fourth reservoirs and said first material is transported toward said third reservoir when pressures are applied to said first and second channels, and (ii) said first material is transported toward said fourth reservoir when the pressure applied to said second channel by said second pressure source is different relative to that applied in condition (i).

22. The apparatus of claim 21 wherein the pressures applied to said first and second channels in condition (i) are substantially the same.

23. The apparatus of claim 21 or 22 wherein the pressure applied to said second channel in condition (ii) is less than that applied to said first channel.

24. An apparatus for effecting microfluidic manipulation comprising:

a first reservoir adapted for containing a first material;

a second reservoir adapted for containing a second material;

a third reservoir adapted for containing a third material;

a fourth reservoir adapted for containing a fourth material;

a first channel having a first end in fluidic communication with said first reservoir;

a second channel having a first end in fluidic communication with said second reservoir;

a third channel having a first end in fluidic communication with said third reservoir;

a fourth channel having a first end in fluidic communication with said fourth reservoir;

said first, second, third, and fourth channels having respective second ends that are interconnected to form a first junction; and transport means operatively connected to said first and second or to said third and fourth channels for effecting transport of the first and second material toward said third and fourth reservoirs;

wherein the first material is transported toward said third and fourth reservoirs and the second material is transported toward said third reservoir such that the first and second materials are mixed in a controlled proportion in the third channel when said transport means is applied to the channels.

25. The apparatus of claim 24 wherein the transport means comprises a source of pressure operatively connected to said first and second channels; and the lengths, cross-sections, or combination thereof, of the first, second, third, and fourth channels are dimensioned such that the first material is transported toward said third and fourth reservoirs and the second material is transported toward said third reservoir such that the first and second materials are mixed in a controlled proportion in the third channel.

26. The apparatus of claim 24 wherein the transport means comprises a subambient pressure source operatively connected to said third and fourth channels; and the lengths, cross-sections, or combination thereof, of the first, second, third, and fourth channels are dimensioned such that the first material is transported toward said third and fourth reservoirs and the second material is transported toward said third reservoir such that the first and second materials are mixed in a controlled proportion in the third channel.

27. The apparatus set forth in claim 24, 25, or 26 wherein the third and fourth reservoirs are formed as a single reservoir.

28. The apparatus set forth in claim 24 comprising:

a fifth reservoir adapted for containing a fifth material;

a sixth reservoir adapted for containing a sixth material;

a fifth channel having a first end in fluidic communication with the fifth reservoir, a second end in fluidic communication with the sixth reservoir;

said fifth channel intersecting with said third channel to form a second junction between the first junction and the third reservoir; and wherein said transport means is operatively connected to said first, second, and fifth channels for effecting transport of the first, second, and fifth materials toward said third, fourth, and sixth reservoirs, the lengths, cross-sections, or combinations thereof, of the channels are dimensioned such that when the transport means is applied to said first, second, and fifth channels, the first material is transported toward said third and fourth reservoirs, the second material is transported toward said third reservoir such that the first and second materials are mixed in controlled proportions in the third channel, and said mixed first and second materials are transported toward the sixth reservoir and the fifth material and the mixed first and second materials are transported toward the third reservoir such that they are mixed in a controlled fashion.

29. The apparatus set forth in claim 24 comprising:

a fifth channel having a first end in fluidic communication with the second reservoir and a second end in fluidic communication with the fourth reservoir;

said fifth channel intersecting with said third channel to form a second junction between the first junction and the third reservoir;

wherein the lengths, cross-sections, or combinations thereof, of the channels are dimensioned such that when the transport means are applied, the first material is transported toward said third and fourth reservoirs, the second material is transported toward said third reservoir such that the first and second materials are mixed in controlled proportions in the third channel, and said mixed first and second materials are transported toward the fourth reservoir through the second junction and the second material and the mixed first and second materials are mixed at the second junction and transported toward the third reservoir such that they are mixed in a controlled fashion.

30. The apparatus set forth in claim 24 comprising:

a fifth reservoir adapted for containing a fifth material;

a sixth reservoir adapted for containing a sixth material;

a fifth channel having a first end in fluidic communication with the fifth reservoir, a second end in fluidic communication with the sixth reservoir;

said fifth channel intersecting with said third channel to form a second junction between the first junction and the third reservoir; and wherein said transport means is operatively connected to said third, fourth, and sixth channels for effecting transport of the first, second, and fifth materials toward said third, fourth, and sixth reservoirs, the lengths, cross-sections, or combinations thereof, of the channels are dimensioned such that when the transport means is applied, the first material is transported toward said third and fourth reservoirs, the second material is transported toward said third reservoir such that the first and second materials are mixed in controlled proportions in the third channel, and said mixed first and second materials are transported toward the sixth reservoir and the fifth material and the mixed first and second materials are transported toward the third reservoir such that they are mixed in a controlled fashion.

31. The apparatus set forth in claim 28 or 30 wherein the third, fourth, and sixth reservoirs are formed as a single reservoir.

32. The apparatus of claim 29 wherein the transport means comprises a source of pressure operatively connected to said first, second, and fifth channels; and the lengths, cross-sections, or combination thereof, of the channels are dimensioned such that the first material is transported toward said third and fourth reservoirs and the second material is transported toward said third and fourth reservoirs such that the first and second materials are mixed in a controlled proportion in the third channel.

33. The apparatus of claim 29 wherein the transport means comprises a sub-ambient pressure source operatively connected to said third, fourth, and fifth channels; and the lengths, cross-sections, or combination thereof, of the channels are dimensioned such that the first material is transported toward said third and fourth reservoirs and the second material is transported toward said third reservoir such that the first and second materials are mixed in a controlled proportion in the third channel.

34. The apparatus of claim 29, 32, or 33 wherein the third and fourth reservoirs are formed as a single reservoir.

35. An apparatus for effecting microfluidic manipulation comprising:

a first reservoir adapted for containing a first material;

a second reservoir adapted for containing a second material;

a third reservoir adapted for containing a third material;

a first channel having a first end in fluidic communication with said first reservoir;

a second channel having a first end in fluidic communication with said second reservoir;

a third channel having a first end in fluidic communication with said third reservoir;

said first and second channels having respective second ends that are interconnected with a second end of said third channel to form a first junction; and transport means operatively connected to said first channel, or to said second and third channels, for effecting transport of the first material from said first reservoir toward said second and third reservoirs;

wherein the lengths, cross-sections, or combinations thereof, of the channels are dimensioned to provide controlled flow of the first material to said second and third channels at said first junction upon application of the transport means to said first channel or to said second and third channels.

36. The apparatus of claim 35 wherein the transport means comprises a source of pressure operatively connected to said first channel.

37. The apparatus of claim 35 wherein the transport means comprises a sub-ambient pressure source operatively connected to said second and third channels.

38. The apparatus of any of claims 35, 36, or 37 wherein the second and third reservoirs are formed as a single reservoir.

39. The apparatus of claim 35 further comprising a fourth reservoir adapted for containing a fourth material;

a fifth reservoir adapted for containing a fifth material;

a fourth channel having a first end in fluidic communication with said fourth reservoir;

a fifth channel having a first end in fluidic communication with said fifth reservoir; and a sixth channel having a first end interconnected with respective second ends of said fourth and fifth channels to form a second junction, said sixth channel having a second end interconnecting with said third channel to form a third junction intermediate said first junction and said third reservoir;

wherein said transport means is operatively connected to said fourth channel, or to said fifth and third channels, for effecting transport of the fourth material from said fourth reservoir toward said fifth and third reservoirs;

wherein, the lengths, cross-sections, or combinations thereof, of the channels are dimensioned to provide controlled flow of the fourth material to said fifth and sixth channels at said second junction and mixing of the first and fourth materials at said third junction upon application of the transport means to said first and fourth channels or to said second, third and fifth channels.

40. The apparatus of claim 39 wherein the transport means comprises a source of pressure operatively connected to said first and fourth channels.

41. The apparatus of claim 39 wherein the transport means comprises a sub-ambient pressure source operatively connected to said second, third, and fifth channels.

42. The apparatus of any of claims 39, 40, or 41 wherein the second, third, and fifth reservoirs are formed as a single reservoir.

\* \* \* \* \*